(12) United States Patent
Gupta

(10) Patent No.: US 7,776,544 B2
(45) Date of Patent: Aug. 17, 2010

(54) EXTRACTION AND QUANTIFICATION OF VITAMINS A & D IN FLUID SAMPLES

(75) Inventor: Rajan Gupta, Edmonton (CA)

(73) Assignee: SciMed Technologies Inc., Edmonton, Alberta (CA)

( * ) Notice: Subject to any disclaimer, the term of this patent is extended or adjusted under 35 U.S.C. 154(b) by 681 days.

(21) Appl. No.: 10/495,660

(22) PCT Filed: Jun. 10, 2003

(86) PCT No.: PCT/CA03/00878

§ 371 (c)(1), (2), (4) Date: Nov. 1, 2004

(87) PCT Pub. No.: WO03/104820

PCT Pub. Date: Dec. 18, 2003

(65) Prior Publication Data

US 2005/0079563 A1   Apr. 14, 2005

(51) Int. Cl.
*G01N 33/53* (2006.01)
(52) U.S. Cl. .................. 435/7.1; 435/7.2; 435/7.91; 435/7.92
(58) Field of Classification Search ............ 436/17, 436/161, 178, 817, 20, 22, 23, 50, 60, 71, 436/819, 822, 824, 825, 904; 435/803, 961, 435/973; 210/634, 635; 426/73, 311, 417, 426/424, 425, 429, 491; 514/167, 168; 552/653; 554/156, 157; 119/14.14; 585/803
See application file for complete search history.

(56) References Cited

U.S. PATENT DOCUMENTS

| | | | | |
|---|---|---|---|---|
| 2,318,749 A | * | 5/1943 | Buxton et al. | 424/554 |
| 2,374,471 A | * | 4/1945 | Buxton | 552/653 |
| 2,404,618 A | * | 7/1946 | Buxton | 514/167 |
| 2,412,561 A | * | 12/1946 | Buxton | 514/725 |
| 3,665,039 A | * | 5/1972 | Ruegg et al. | 568/497 |
| 4,237,118 A | * | 12/1980 | Howard | 424/630 |
| 4,585,741 A | * | 4/1986 | Clevinger et al. | 436/542 |
| 4,690,890 A | * | 9/1987 | Loor et al. | 435/7.21 |
| 4,923,819 A | * | 5/1990 | Fernandez et al. | 436/518 |
| 5,232,836 A | | 8/1993 | Bouillon et al. | |
| 5,312,978 A | * | 5/1994 | Mori et al. | 562/510 |

OTHER PUBLICATIONS

Hollis, B.W. & Frank, N.E. Quantitation of vitamin D2, vitamin D3, 25-hydroxyvitamin D2, and 25-hydroxyvitamin D3 in human milk. Methods Enzymol. 1986;123:167-176.*
O'Keefe, S.F. Nomenclature and classification of lipids, in Food Lipids, Chapter 1, pp. 1-36, Akoh, C.C. & Min, D.B., Eds., Marcel Dekker, Inc. (1998).*
Shahidi, F. & Wanasundara, J.P.D. Extraction and analysis of lipids, in Food Lipids, Chapter 5, pp. 115-136, Akoh, C.C. & Min, D.B., Eds., Marcel Dekker, Inc. (1998).*
Li, Y. & Watkins, B.A. Analysis of fatty acids in food lipids, in Current Protocols in Food Analytical Chemistry, Unit D1.2, pp. D1.2.1 to D1.2.15, Wrolstad, R.E. et al., Eds., John Wiley & Sons, Inc. (2001).*
Flick, E.W. Industrial solvents handbook, 5d., Appendix—Comparative data for various solvents, pp. 938-948, Noyes Data Corporation (1998).*
Kobayashi, N. et al. A selective immunoaffinity chromatography for determination of plasma 1,25-dihydroxy-vitamin D3: Application of specific antibodies raised against a 1,25-dihydroxy-vitamin D3-bovine serum albumin conjugate linked through the 11(alpha)-position. Anal. Biochem. 1997;244:374-383.*
van den Berg, H. et al. Determination of vitamin D in fortified and nonfortified milk powder and infant formula using a specific radioassay after purification by high-performance liquid chromatography. J. Agric. Food Chem. 1986;34:264-268.*
Vining, R.F. et al. Steroid radioimmunoassay—Effect of shortened incubation time on specificity. Clin. Chem. 1981;27:910-913.*
Writz et al. (Journal of Lipid Research 1981 vol. 22, p. 869-871).*
Harlow et al. ("Antibodies a Laboratory Manual," Cold Spring Harbor, NY, Cold Spring Harbor Laboratory Press, 1988, p. 141-155).*
Granado, F. et al.; "A fast, reliable and low-cost saponification protocol for analysis of carotanoids in vegetables." Journal of Food Composition and Analysis, vol. 14, No. 5, Oct. 20, 2001 pp. 479-489 XP002255154.

(Continued)

*Primary Examiner* — Jacob Cheu
(74) *Attorney, Agent, or Firm* — Bennett Jones LLP

(57) ABSTRACT

The invention discloses monoclonal antibodies for vitamins A (retinol palmitate) and D3 (cholecalciferol); a method for using monoclonal antibodies, and the monoclonal antibodies disclosed herein, in particular, to quantitate these vitamins in fluids such as dairy products, and blood, and also raw or processed agri-food and beverage products. The method involves contacting the sample with a mixture of polar and non-polar organic solvents in combination with inorganic salts to remove fat molecules into an organic fraction, and assaying the organic fraction by immunoassay involving the monoclonal antibodies. The presence of a mixture of non-polar and polar organic solvents increases the separation of vitamins from fat molecules and enables the test samples to be quantified by immunoassay without any further treatment.

10 Claims, No Drawings

OTHER PUBLICATIONS

Bouillon, et al., "2 Direct Nonchromatographic Assays for 25 Hydroxyvitamin D", Clinical Chemistry, vol. 30, No. 11, 1984, pp. 1731-1736, XP009017492.

Tanner, et al., "Survey of Vitamin Content of Fortified Milk" Journale of the Association of Official Analytical Chemists, vol. 71, No. 3, 1988, pp. 607-610, XP009017609.

Kobayashi, et al., Production and Characterization of Monoclonal Antibodies Against A Novel 1a, 25-Dihydroxyvitamin D3-Bovine Serum Albumin Conjugate Linked through the 11a-Position, Journal Steroid Biochemistry, vol. 63. No. 1-3, pp. 127-137, 1997.

Jean, et al., Production and Characterization of Polyclonal Antibodies Against Cholecalciferol (vitamin D3), Journal of Immunological Methods, 1999, pp. 155-163.

Zhou, et al., "Production of a Hybridoma Cell Line Secreting Retinoic Acid-Specific Monoclonal Antibody", Journal of Immunological Methods, 138 (1991) pp. 211-223.

Sharpless, et al., "Value Assignment of Retinol, Retinvl Palmitate, Tocopherol, and Carotenoid Concentrations, etc." Journal of AOAC International vol. 82, No. 2, 1999, pp. 288-296.

* cited by examiner

EXTRACTION AND QUANTIFICATION OF VITAMINS A & D IN FLUID SAMPLES

FIELD OF THE INVENTION

The present invention relates to methods for extracting and quantifying fat-soluble vitamins from fluid samples. In particular, it relates to antibodies, methods for their use, and kits therefore, to quantify vitamins A and D in dairy products and in other fluids.

BACKGROUND OF THE INVENTION

Milk which is marketed in Canada and the United States must be fortified with vitamin A and D3 (1,2). Regulatory agencies have set standards specifying the minimum amount of vitamins A and D3 to be added to milk products. Fortified fluid milk products add value to the agricultural and dairy industry in that consumers seek products with essential vitamins and nutrients. Milk processors typically assert general claims of vitamin fortification levels because current methodology is too costly and time consuming to implement testing on a batch basis.

Vitamins A and D3 are potentially toxic to humans at higher concentrations. Since the margin between the nutritionally desirable intake of vitamins and harmful excess is small (3,4,5) it is important that errors in fortification levels be detectable in the shortest possible time. Currently available methodology for these analyses is laborious, tedious, and expensive, and adds to the high cost of production to dairy processors. Currently available methods for detecting vitamin A and D3 metabolites include binding assays, receptor proteins, high performance liquid chromatography (HPLC), and gas chromatography-mass spectrometry (GC-MS) (6,7,8,9). Such analyses in any laboratory are time consuming, require skill and expertise on the part of analysts, and require large capital investments for equipment.

Vitamins A and D3 are fat soluble and they are bound by fat molecules in a dairy product such as milk. Accordingly, they must be extracted in lengthy extraction steps. Since vitamins A and D are both labile to heat, light, and oxidation, laborious extraction results in loss of the vitamin in the preparative steps, and often requires 3 to 5 days for the completion of the analyses.

Vitamin D plays an active role in the homeostatic mechanism that controls the concentration of calcium ion in plasma. Vitamin D is transported to various sites in the body where it is activated. The activated forms of the vitamin act on the target tissues, thereby causing an increase in calcium content. The activation of vitamin D is regulated in a negative feedback system by plasma calcium. The most biologically active form of vitamin D is 1,25-dihydroxycholecalciferol or calcitriol, which is formed by two successive hydroxylations of vitamin D. That is, calcitriol is formed by the sequential hydroxylation of vitamin D at C-25 in the liver and at C-1 in the kidney. Various other analogs can be produced by hydroxylation at C-24 and C-26. The above mentioned biologically active forms of hydroxylated vitamin D are synthesized in the body only and are not found in dairy or agri-food products. Vitamin D3, or cholecalciferol, is the form used as an additive and is also produced in the body when the skin, which contains the provitamin 7-dehydrocholesterol, is exposed to sunlight.

Currently, the principal assay for Vitamin D3 in dairy samples which has been developed is a two step high pressure liquid chromatography (HPLC) assay, whereby the extracted vitamin in about 200 ml of the hexane is lyophilized to about 2 ml and the fraction corresponding to vitamin D is isolated by HPLC and collected manually. This collected fraction of vitamin D is again lyophilized, and dissolved in about 0.5 ml of methanol and loaded again on reverse phase HPLC. This assay employs an expensive and costly laboratory set up and requires trained and skilled personnel to handle advanced instrumentation like HPLC (8,9,10).

The principal assays for vitamin A include laborious extractions and the use of HPLC, or a direct extraction with the detection of vitamin A by spectrofluorometer. The latter process has limitations due to the interference from other compounds that has fluorescence at the same wavelength. Moreover, because vitamins A and D3 are sensitive to UV-light, they might lose some of their activity due to extensive extractions, purifications and storage conditions.

The standard assays, which employ one or two step (HPLC) are illustrated, for example, by references (6-9) and (10).

Therefore, there is a need in the art for methods and kits for quantifying vitamins A and D in a fluid sample, and dairy products in particular.

SUMMARY OF THE INVENTION

This invention discloses methods for quantifying the level of vitamins A and D3 in fluids, such as dairy products and blood or other bodily fluids. The methods disclosed herein comprise the extraction of a fluid sample with an extraction solvent to isolate fat-soluble vitamins A and D3 from the rest of the fluid mixture. The vitamins are then quantified with assays which may include using antibodies to vitamins A and D3. Either monoclonal or polyclonal antibodies may be used.

The method would allow dairy processors to test for Vitamins A and D3 internally and obtain a result within few hours, so that the percentage of recommended daily amounts of vitamin D contained in the product tested can be indicated directly on the package of milk or other dairy product containing the product. In one aspect, the invention comprises a method of quantifying vitamin A or D3, or vitamin A and D3, in a fluid sample, comprising the steps of:

(a) extracting the fluid sample with an inorganic salt and an extraction solvent comprising a mixture of a non-polar organic solvent and a polar organic solvent, to produce an organic fraction; and (b) determining the amount of vitamin D3 or vitamin A, or both vitamin D3 and vitamin A, in the organic fraction.

In one embodiment, the amount of vitamin D3 and/or vitamin A is determined using a monoclonal antibody to vitamin D3 and/or vitamin A respectively. The antibody may be used in a competitive ELISA or a sandwich ELISA to quantify the vitamin of interest. Isolated cell lines that synthesize the monoclonal antibody to vitamin A and vitamin D3 are described herein. In other embodiments, direct measurement assays may be utilized.

In yet another aspect, this invention is a kit comprising a monoclonal antibody, said kit being used to detect vitamin D3 or vitamin A, or both vitamin D3 and vitamin A in a sample, which may include any fluid such as those described herein. The kit may include means for quantifying the vitamin which may include assay reagents, glassware and plasticware.

DETAILED DESCRIPTION OF PREFERRED EMBODIMENTS

The present invention provides a method of quantifying fat-soluble vitamins, provitamins and their metabolites in a fluid. In one embodiment, the method is applied to vitamins A and D3 present in a dairy product such as milk. Generally, the method comprises the steps of providing an antibody that specifically binds to the fat-soluble vitamin, which is preferably a monoclonal antibody, extracting the vitamin from the fluid using an extraction solvent, and assaying the vitamin extracted from the fluid.

In this application, the sample fluid is preferably a fluid dairy product such as milk, but may also include, without limitation, other dairy products, an agri-food, a beverage, blood or other biological fluids.

In one embodiment, the assay methods of the present invention utilize antibodies to vitamin D3 and vitamin A, which are preferably monoclonal antibodies. Accordingly, the invention may further comprise the generation and purification of a monoclonal antibody against vitamin D3 or other forms of vitamin D. The monoclonal antibody which specifically binds to vitamin D3 does not exhibit significant or substantial binding activity to other variants or biologically active forms of vitamin D. As used herein, vitamin D, also known as calciferol, includes all available forms of vitamin D including vitamin D3 also known as cholecalciferol. As well, the present invention comprises the generation and purification of a monoclonal antibody against vitamin A. As used herein, vitamin A, also known as retinol palmitate, includes all active forms of vitamin A and provitamin A carotenoids. The monoclonal antibody is of course distinct from the commercially available polyclonal antibody of vitamin A.

Methods for preparing and isolating polyclonal and monoclonal antibodies are well known in the art. See, for example, Current Protocols in Immunology, Cooligan, et al. (eds.), National Institutes of Health, John Wiley and Sons, Inc., 1995; Sambrook et al., Molecular Cloning: A Laboratory Manual, Second Edition, Cold Spring Harbor, N.Y., 1989; and Hurrell, J. G. R., Ed., Monoclonal Hybridoma Antibodies: Techniques and Applications, CRC Press, Inc., Boca Raton, Fla., 1982. As would be evident to one of ordinary skill in the art, polyclonal antibodies can be generated from a variety of warm-blooded animals, such as horses, cows, goats, sheep, dogs, chickens, rabbits, mice, and rats with Vitamin A or D.

The present invention comprises monoclonal antibodies which specifically bind to vitamin A, as well as monoclonal antibodies which specifically bind to vitamin D3. These monoclonal antibodies are not known in the prior art. In general terms, commercially available pure vitamin A or vitamin D3 may be conjugated to keyhole limpet hemocyanin and used to immunize mice. Spleen cells may be recovered from the immunized mice and fused with known cell lines. Those hybridomas which produce the desired monoclonal antibody may be detected by ELISA. These procedures are well known and include standard techniques available to one skilled in the art.

As used herein, the term "antibodies" includes polyclonal antibodies, affinity-purified polyclonal antibodies, monoclonal antibodies, and antigen-binding fragments, such as F(ab').sub.2 and Fab proteolytic fragments. Genetically engineered intact antibodies or fragments, such as chimeric antibodies, Fv fragments, single chain antibodies and the like, as well as synthetic antigen-binding peptides and polypeptides, are also included.

Antibodies are determined to be specifically binding if: 1) they exhibit a threshold level of binding activity, and/or 2) they do not significantly cross-react with related molecules. Antibodies described herein specifically bind if they bind to either Vitamin A or Vitamin D3 with a binding affinity ($K_a$) of $10^6$ $M^{-1}$ or greater preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art (Scatchard, G., Ann. NY Acad. Sci. 51: 660-672, 1949).

The methods of the present invention utilize an extraction solvent which comprises organic solvents with high selectivity in extracting polar compounds from fat molecules. In one embodiment, the extraction solvent comprises a polar organic solvent and a non-polar organic solvent in combination with an inorganic salt, to extract fat-soluble compounds from fluids, such as dairy products. As used herein, an "organic solvent" includes, without limitation, liquid aliphatic hydrocarbons preferably containing 4 to 10 carbon atoms, or halogenated hydrocarbons containing 1 to 4 carbon atoms. Preferred inorganic salts include alkaline metal salts such as potassium hydroxides, chlorides, carbonates or phosphates. The inorganic salt is preferably dissolved in an alcoholic solution, such as a 65% ethanol solution. It is preferred that the fluid sample have an alkaline pH for the extraction. The use of a potassium or sodium hydroxide salt of course produces suitable alkaline conditions.

Solvent polarity has been defined and measured in several different ways, one of the most common being the dielectric constant ($\epsilon$). Aliphatic hydrocarbon solvents typically have dielectric constant values less than about 2.0. As used herein, "non-polar" shall refer to any solvent having a dielectric constant less than 3.0, and preferably less than about 2.0. Halogenated hydrocarbon solvents typically have dielectric constants greater than about 8.0. As used herein, "polar" shall refer to any organic solvent having a dielectric constant greater than 3.0, and preferably greater than about 4.0, and more preferably greater than about 8.0.

In one embodiment, the extraction solvent comprises a mixture of hexane and petroleum ether as the non-polar solvent and methylene chloride (dichloromethane) as the polar solvent. Preferably, equal amounts of hexane and petroleum ether are mixed with a small amount of methylene chloride. In one embodiment, the solvent comprises hexane, petroleum ether and methylene chloride in a 49:49:2 ratio (49:1 non-polar to polar).

Suitable non-polar solvents may include butane, pentane, hexane, heptane and octane, including mixtures thereof such as petroleum ether, benzene and acetonitrile, amongst others. Suitable polar organic solvents may include chloroalkanes such as methylene chloride and ethyl acetate. Suitable inorganic salts may include potassium chloride, potassium hydroxide, or sodium hydroxide, sodium bicarbonate, and sodium ascorbate. It is preferred that the salt raise the pH of the fluid sample to an alkaline pH.

The volume ratio of non-polar to polar in the extraction solvent may be greater than 2:1, and is preferably greater than 5:1, and is most preferably greater than about 10:1.

The extraction solvent may be used in ratio of 1:1 or lower with the fluid. In one embodiment, 20 ml of a milk sample may be extracted with 15 ml of the preferred extraction solvent described herein. Optionally, an antioxidant such as pyrogallol may be added to the fluid to prevent oxidation of the vitamins A and D3 during the extraction procedure.

The mixture of organic solvents in combination with inorganic salts has the ability to extract fat-soluble compounds that can be directly detected by immunoassay without any further treatment. The extracted vitamins can be quantified directly by well-known enzyme-immunoassays, such as by a competitive ELISA, a sandwich ELISA or by radioimmunoassay, which are standard quantitative assays well known in the art (Persoon T. Immunochemical assays in the clinical laboratory. Clinical Laboratory Science; 5(1): 31-40, 1992).

The extracted vitamins and antibodies can be used for detection and quantification of vitamins A and D3 by direct measurement. The Fourier Transform-Infrared Spectroscopy (FT-IR) method is well known and may be applied through incorporation to biochip technology in the present invention. FT-IR is a non-destructive technique that enables the identification of the unique chemical bonds (a "fingerprint") of a given organic substance, as each chemical bond in a molecule absorbs different frequencies at a different wave number. A molecular fingerprint of the protein/vitamin complex in solution may be obtained, in terms of infrared spectra. This spectrum is a unique identity of the protein/vitamin complex at a given concentration in solution. Other direct measurement techniques are well-known in the art.

The methods and antibodies disclosed herein can also be used to prepare a kit that can be used to determine the levels of vitamins A and D3 in a sample. In one embodiment, the kit comprises an extraction solvent for extraction of the vitamins from the fluid sample, a sample of the monoclonal antibody, and the reagents required for the assay, which may be an ELISA assay. The kit may additionally comprise hardware, required to perform the analysis, such as tubes, assay plates or other glassware or plasticware.

While the invention has been described in conjunction with the disclosed embodiments, it will be understood that the invention is not intended to be limited to these embodiments. On the contrary, the invention is intended to cover alternatives, modifications and equivalents, which may be included within the spirit and scope of the invention as defined by the appended claims.

The following examples are intended only to illustrate and describe the invention rather than limit the claims that follow.

EXAMPLES

Materials and Methods

All chemicals were purchased from Sigma Chemical Company (St. Louis, Mo.) unless otherwise noted. Vitamin D3 (Cholecalciferol) was from Merck. Hexane, petroleum ether, methylene chloride, potassium hydroxide were from Caledon Laboratories. Bovine serum albumin was from Gibco BRL, and TMB substrate was from KPL Laboratories.

Generation and Identification of Monoclonal Antibodies

1. Conjugation of Retinol Palmitate to Keyhole Limpet Hemocyanin (KLH)

4.1 mg of vitamin A (retinol palmitate) was mixed with KLH and stirred overnight at room temperature. After dialysis, glutaraldehyde was added to the mixture to a final concentration of 1%. The resulting mixture was stirred for 6 hrs. The conjugated mixture was dialysed in phosphate buffered saline (pH 7.4) for 4 hr. Conjugated KLH-vitamin A was filter sterilized and stored in sterile vials at −20° C.

2. Conjugation of Vitamin D3 to Keyhole Limpet Hemocyanin (KLH)

5.4 mg of vitamin D3 was mixed with 10 mg of KLH and stirred overnight at room temperature. After dialysis, glutaraldehyde was added to the mixture to a final concentration of 1%. The resulting mixture was stirred for 6 hrs. The conjugated mixture was dialysed in phosphate buffered saline (pH 7.4) for 4 hr. Conjugated KLH-vitamin D3 was filter sterilized and stored in sterile vials at −20° C.

3. Immunization and Hybridoma Production for vitamin A

For general procedures related to the generation of monoclonal antibodies, refer to Harlow and Lane, Antibodies—A Laboratory Manual, Cold Spring Harbor Laboratory, 1988. BALB/c mice were immunized, via intraperitoneal injection, with 50 μg/mouse of the vitamin A-KLH conjugate emulsified in complete Freund's adjuvant. After two weeks, a second injection of the antigen was given in Freund's incomplete adjuvant, followed by another dose of the antigen in sterile PBS (pH-7.4), after three days. An intrasplenic injection of the antigen was given 10 days following the third dose of antigen. Three days after the intrasplenic injection, spleen cells from the mice were isolated and fused with the Sp2/0-Ag 14 cell line as described by Shulman et al. in Nature 276: 269 (1978) using the method of Galfre et al., disclosed in Nature 266: 550 (1977). Cells were cultured in 96-well tissue culture plates in RPMI media supplemented with 20% fetal bovine serum. After 24 hrs, selection medium HAT (hypoxanthine, aminopterin and thymidine) was added as described by J. W. Littlefield in Science 145: 709 (1964).

4. Elisa with Monoclonal Antibody to Vitamin A

Monoclonal antibodies that bind to vitamin A were detected from culture supernatants by using ELISA. Microtitre plates Falcon) were coated with retinol palmitate (20 ug/ml in PBS, pH 7.4) and incubated at 4° C. overnight. Plates were washed with PBS (pH 7.4) and blocked with 3% bovine serum albumin for 3 hrs. Plates were washed again with PBS, and air-dried. Wells exhibiting hybridoma growth were marked and the supernatant (100 ul) from each well was transferred to the vitamin A coated plate and incubated overnight at 4° C. Commercially available polyclonal antibody for vitamin A, and anti-sera collected as blood from tail vein of the mice after the third intraperitoneal injection of vitamin A (positive control representing the high titre antibody against vitamin A), were run concurrently as controls. Pre-bleed sera (collected as blood from tail vein of the mice before the vitamin A injection) were also run concurrently as negative control. Bound monoclonal antibody was detected with enzyme-labeled antibody (1:6,000 dilution, Sigma) using TMB as substrate.

Cells from positive wells were transferred to 24-well plates followed by 6-well plates and then into T25 tissue culture flasks. The cell lines producing high titre of antibody are SM-1.4A and SM-4.12A.

5. Immunization and Hybridoma Production for Vitamin D3

For general procedures related to the generation of monoclonal antibodies, refer to Harlow and Lane, Antibodies—A Laboratory Manual, Cold Spring Harbor Laboratory, 1988. BALB/c mice were immunized, via intraperitoneal injection, with 50 μg/mouse of the vitamin D-KLH conjugate emulsified in complete Freund's adjuvant. After two weeks, a second injection of the antigen was given in Freund's incomplete adjuvant, followed by another dose of the antigen in sterile PBS (pH-7.2), after three days. An intrasplenic injection of the antigen was given 10 days following the third dose of antigen. Three days after the intrasplenic injection, spleen cells from the mice were isolated and fused with the Sp2/0-Ag 14 cell line as described by Shulman et al. in Nature 276: 269 (1978) using the method of Galfre et al., disclosed in Nature 266: 550 (1977). Cells were cultured in 96-well tissue culture plates in RPMI media supplemented with 20% fetal bovine serum.

After 24 hrs, selection medium HAT (hypoxanthine, aminopterin and thymidine) was added as described by J. W. Littlefield in Science 145: 709 (1964).

6. ELISA with Monoclonal Antibody to Vitamin D3

Monoclonal antibodies that bind to vitamin D3 were detected from culture supernatants by using ELISA. Microtitre plates (Falcon) were coated with vitamin D3 (20 ug/ml in PBS, pH 7.4) and incubated at 4° C. overnight. Plates were washed with PBS (pH 7.4) and blocked with 3% bovine serum albumin for 3 hrs. Plates were washed again with PBS, and air-dried. Wells exhibiting hybridoma growth were marked and the supernatant (100 ul) from each well was transferred to the vitamin D3 coated plate and incubated overnight at 4° C. Commercially available monoclonal antibody for 1-25 dihydroxy vitamin D3 and anti-sera collected as blood from tail vein of the mice after the third intraperitoneal injection of vitamin D3 (positive control representing a high titre antibody against vitamin D3), were run concurrently as positive controls. Pre-bleed sera (collected as blood from tail vein of the mice before the vitamin D3 injection) were also run concurrently as negative control. Bound monoclonal antibody was detected with enzyme-labeled antibody (1:6,000 dilution, Sigma) using TMB as substrate.

Cells from positive wells were transferred to 24-well plates, followed by 6-well plates and then into T25 tissue culture flasks. The cell lines producing high titre of antibody are SM 4.9A, SM 4.9B and SM 1.1E.

Extraction of Vitamins A and D3 from Milk 20 ml of well-mixed fluid milk, at room temperature, was placed into amber colored bottle, followed by addition of 2 ml of 10% pyrogallol antioxidant, and mixed for 5 min. Then slowly from the sides of the bottle, cold alcoholic potassium hydroxide solution was added to achieve a ratio of potassium, ethanol and water of 1:2:0.3. Samples were placed in the incubator, and extracted with 15 ml of a mixture of organic solvents. The solvent mixture comprised hexane: petroleum ether: methylene chloride, in a ratio of 49:49:2. The sample was then either centrifuged or placed on the table for 10 min, to separate the phases. The supernatant may be used directly for immunoassay for the quantification of vitamins A & D3.

Quantification of Vitamin A and D3 in Dairy Samples Using ELISA

Conventional assays utilizing monoclonal or polyclonal antibodies for vitamin D (including its metabolites and analogs) and vitamin A (including precursors or provitamins, metabolites and analogs) are well known in the art. Such assays include competitive binding assays and enzyme-linked immunoassays which are well known in the art. For example, methods to assay for 1,25-dihydroxyvitamin D are described (11) in Chen et al., J. Nutr. Biochem. 1:320-327 (1990), and in U.S. Pat. Nos. 4,297,289, 4,816,417, 4,585,741 and 5,232,836.

REFERENCES

The following references are cited in the application as numbers in brackets [( )] at the relevant portion of the application. In addition, there are references cited within this application. Each of these references, whether cited in the body of this application or below, is incorporated herein by reference.

1. The Food and Drugs Act and Regulations; Department of National Health and Welfare, Section B.08.003 to B.08.006; Jul. 10, 1991
2. Grade "A" Pasteurized Milk Ordinance, U.S. Department of Health and Human Services, Public Health Service; Food and Drug Administration; 1995 Revision
3. Kirschmann, G & J, Nutrition Almanac 4$^{th}$ ed. New York: McGraw Hill, 1996
4. Reinhold Veith, Vitamin D Supplementation, 25-hydroxyvitamin D concentrations, and safety 1, 2; American Journal of Clinical Nutrition, Vol. 69, No. 5, 842-856, May 1999
5. Blank, S., Scanlon, K. S., Sinks, T. H., Let, S., and Falk, H. An outbreak of hypervitaminosis D associated with the overfortification of milk from a home delivery dairy. American J. Publ. Health, 855, 656-659, 1995
6. Silva, MG, and Sanders J K, Vitamin D in Infant Formula and Enteral Products by Liquid Chromatography: Collaborative Study, J. AOAC Int., January-February 1996; 79 (1): 73-80
7. Kurmann, A, and Indyk, H, Endogenous Vitamin D Content of Bovine Milk: Influence of Season, Food Chem., 50 (1): 75-81, 1994
8. Agarwal, V K, Liquid Chromatographic Determination of Vitamin D in Animal Feeds and Premixes, J. AOAC Int., 75: (5): 812-815, 1990
9. Vitamin D in fortified milk and milk powder; Liquid chromatographic method; AOAC Official Methods of Analysis; 15$^{th}$ ed., 1068-1069, 1990
10. Method for the analysis of vitamins A & D in milk, U.S. Department of Health and Human Services, Public Health Service; Food and Drug Administration—LQAB A & D; 1995 Revision
11. Chen, T. C., Turner, A. K., and Holick, M. F. A method for the determination of circulating concentration of 1,25-dihydroxyvitamin D, J. Nutr. Biochem., 1, 1990.

I claim:

1. A method of quantifying vitamin A or D3, or vitamins A and D3, in an aqueous dairy sample within a few hours, comprising the steps of:
   (a) extracting the aqueous dairy sample with an alkaline metal salt and an extraction solvent comprising a mixture of a non-polar organic solvent and a polar organic solvent, to isolate vitamin A or D3, or vitamins A and D3 from the aqueous dairy sample into an organic fraction; and
   (b) determining the amount of vitamin D3 or vitamin A, or both vitamin D3 and vitamin A, in the organic fraction, wherein the vitamin is quantified with a monoclonal antibody which specifically binds to the vitamin, and wherein the non-polar organic solvent comprises an aliphatic hydrocarbon having from 4 to 10 carbon atoms, or a mixture thereof, and the polar organic solvent comprises a chloroalkane or ethyl acetate.

2. The method of claim 1 wherein the inorganic alkaline metal salt is added to the sample in an alcoholic solution.

3. The method of claim 2 wherein the alcoholic solution comprises greater than about 50% and less than about 75% ethanol in water (v:v).

4. The method of claim 1, wherein the alkaline metal salt is selected from potassium hydroxide, potassium chloride, sodium hydroxide, sodium bicarbonate or sodium ascorbate.

5. The method of claim 1 wherein the non-polar organic solvent comprises a mixture of hexane and petroleum ether and the polar organic solvent comprises methylene chloride.

6. The method of claim 1 wherein the vitamin D3 or vitamin A, or vitamins D3 and vitamin A, is detected by an immunosorbent assay.

7. The method of claim 1 wherein the vitamin is quantified by direct measurement.

8. The method of claim 4 wherein the alkaline metal salt comprises potassium hydroxide.

9. The method of claim 1, wherein the non-polar organic solvent is selected from butane, pentane, hexane, heptane, octane, or a mixture thereof.

10. The method of claim 1, wherein the chloroalkane is methylene chloride.

* * * * *